(12) United States Patent
Schnell et al.

(10) Patent No.: US 11,493,323 B2
(45) Date of Patent: Nov. 8, 2022

(54) INFRARED-OPTICAL HYBRID IMAGING TECHNOLOGY FOR ALL-DIGITAL HISTOPATHOLOGY

(71) Applicants: The Board of Trustees of the University of Illinois, Urbana, IL (US); Asociación Centro De Investigación Cooperativa en Nanociencias, CIC Nanogune, Donostia-San Sebastián (ES)

(72) Inventors: Martin Schnell, Berlin (DE); Paul Scott Carney, Pittsford, NY (US); Rohit Bhargava, Urbana, IL (US)

(73) Assignees: The Board of Trustees of the University of Illinois, Urbana, IL (US); Asociación Centro De Investigación Cooperativa, Donostia-San Sebastian (ES)

( * ) Notice: Subject to any disclaimer, the term of this patent is extended or adjusted under 35 U.S.C. 154(b) by 0 days.

(21) Appl. No.: 16/733,610

(22) Filed: Jan. 3, 2020

(65) Prior Publication Data
US 2020/0217643 A1    Jul. 9, 2020

Related U.S. Application Data

(60) Provisional application No. 62/787,927, filed on Jan. 3, 2019.

(51) Int. Cl.
*G01N 21/47*       (2006.01)
*G01B 9/02091*   (2022.01)
(Continued)

(52) U.S. Cl.
CPC ........ *G01B 9/02091* (2013.01); *A61B 5/0066* (2013.01); *G01B 9/02004* (2013.01);
(Continued)

(58) Field of Classification Search
CPC ............ G01B 9/02091; G01B 9/02029; G01B 9/02004; G01B 2290/45; G01N 21/4795;
(Continued)

(56) References Cited

U.S. PATENT DOCUMENTS 5,781,294 A * 7/1998 Nakata ............... G01N 21/1702
                                                                    356/487
7,738,115 B2 * 6/2010 Ocelic ................... B82Y 20/00
                                                                    356/501

(Continued)

OTHER PUBLICATIONS

Dazzi, et al., "AFM-IR: Technology and Applications in Nanoscale Infrared Spectroscopy and Chemical Imaging," Chemical Reviews 117, 5146-5173, Dec. 13, 2016.
(Continued)

*Primary Examiner* — Jonathan M Hansen
(74) *Attorney, Agent, or Firm* — Sunstein LLP

(57) ABSTRACT

Methods and apparatus are provided for imaging a response of a sample to radiative heating. A method in accordance with one embodiment has steps of: illuminating a first area of the sample with a radiative heating beam; illuminating a portion of the first area with a probe beam; collecting light exiting the sample due to interaction of the probe beam with the sample; superimposing the light exiting the sample with a reference beam derived from the probe beam, wherein the reference is characterized by an optical phase relative to the probe beam; detecting a spatial portion of the light exiting the sample and the reference beam with at least one detector to generate an interference signal; and processing the interference signal to obtain an image of the sample associated with absorption of the radiative heating beam.

60 Claims, 5 Drawing Sheets
(4 of 5 Drawing Sheet(s) Filed in Color)

(51) Int. Cl.
  *G01B 9/02004* (2022.01)
  *A61B 5/00* (2006.01)
  *G01B 9/02015* (2022.01)

(52) U.S. Cl.
  CPC ..... *G01B 9/02029* (2013.01); *G01N 21/4795* (2013.01); *G01B 2290/45* (2013.01)

(58) Field of Classification Search
  CPC ....... G01N 21/3581; G01N 2021/1731; G01N 21/4788; G01J 3/42; A61B 5/0066; A61B 5/0507
  See application file for complete search history.

(56) References Cited

U.S. PATENT DOCUMENTS

| | | | |
|---|---|---|---|
| 8,001,830 | B2 | 8/2011 | Dazzi et al. |
| 8,739,311 | B2 | 5/2014 | Wickramasinghe et al. |
| 9,091,594 | B2 | 7/2015 | Furstenberg et al. |
| 9,841,324 | B2 | 12/2017 | Furstenberg et al. |
| 10,845,248 | B1 | 11/2020 | Cheng et al. |
| 2009/0302358 | A1* | 12/2009 | Mao .................. H01L 31/03529 257/292 |
| 2013/0292571 | A1 | 11/2013 | Mukherjee et al. |
| 2018/0088041 | A1 | 3/2018 | Zhang et al. |
| 2018/0180642 | A1 | 6/2018 | Shetty et al. |
| 2018/0246032 | A1 | 8/2018 | Li et al. |
| 2018/0259553 | A1 | 9/2018 | Yang et al. |
| 2019/0120753 | A1 | 4/2019 | Prater et al. |
| 2020/0025677 | A1* | 1/2020 | Prater ....................... G01J 3/28 |

OTHER PUBLICATIONS

Dazzi, et al., "AFM-IR: Combining Atomic Force Microscopy and Infrared Spectroscopy for Nanoscale Chemical Characterization," Applied Spectroscopy, vol. 66, No. 12, pp. 1365-1384 (2012).

Lu, et al., "Tip-enhanced infrared nano spectroscopy via molecular expansion force detection," Nature Photonics, vol. 8, pp. 307-312, Jan. 19, 2014.

Nowak, et al., "Nanoscale chemical imaging by photoinduced force microscopy," Science advances 2, 9 pgs., Mar. 25, 2016.

Keilmann, et al., "Near-field microscopy by elastic light scattering from a tip," Philosophical Transactions of the Royal Society of London. Series A: Mathematical, Physical and Engineering Sciences, vol. 362, No. 1817, pp. 787-805, Apr. 15, 2004.

Furstenberg, et al., "Chemical imaging using infrared photothermal microspectroscopy," SPIE Defense, Security, and Sensing vol. 8374, 10 pgs., 2012.

Zhang, et al., "Depth-resolved mid-infrared photothermal imaging of living cells and organisms with submicrometer spatial resolution," Science advances 2, 7 pgs., Sep. 28, 2016.

Sullenberger, et al., "Spatially-resolved individual particle spectroscopy using photothermal modulation of Mie scattering," Optics Letters, vol. 42, No. 2, pp. 203-206, Jan. 5, 2017.

Bai, et al., "Ultrafast chemical imaging by widefield photothermal sensing of infrared absorption," Science Advances 5, eaav7127, 8 pgs., Jul. 19, 2019.

Li, et al., "Mid-Infrared Photothermal Imaging of Active Pharmaceutical Ingredients at Submicrometer Spatial Resolution," Analytical Chemistry, 2017, 89 (9), pp. 4863-4867, Apr. 11, 2017.

A. Gaiduk, et al., "Room-Temperature Detection of a Single Molecule's Absorption by Photothermal Contrast," Science, vol. 330, Issue 6002, pp. 353-356, Oct. 15, 2010.

Mërtiri, et al., "Label Free Mid-IR Photothermal Imaging of Bird Brain With Quantum Cascade Laser," Proceedings of Conference on Lasers and Electro-Optics, San Jose, CA,; Optical Society of America: Washington, DC, 2014; p. AF1B.4, 2 pgs., Jun. 8-13, 2014.

Li, et al., "Super-resolution Mid-infrared Imaging using Photothermal Microscopy," Proceedings of Conference on Lasers and Electro-Optics, San Jose, CA, Optical Society of America: Washington, DC, 2 pgs., Jun. 5-10, 2016.

Mërtiri, et al., "Mid-infrared photothermal heterodyne spectroscopy in a liquid crystal using a quantum cascade laser," Applied Physics Letters 101, 044101, 5 pgs., Jul. 23, 2012.

* cited by examiner

INFRARED-OPTICAL HYBRID IMAGING TECHNOLOGY FOR ALL-DIGITAL HISTOPATHOLOGY

The present application claims priority to U.S. Provisional Application Ser. No. 62/787,927, entitled "Infrared-Optical Hybrid Imaging Technology for All-Digital Histopathology" and filed on Jan. 3, 2019. The foregoing application is incorporated herein in its entirety by reference.

This invention was made with government support under grant R01EB009745 awarded by the National Institutes of Health. The government has certain rights in the invention.

TECHNICAL FIELD

The present invention relates to apparatus and methods for medical imaging, and, more particularly, to apparatus and methods for obtaining images of photothermal response due to absorption, by a sample, of infrared or terahertz radiation.

BACKGROUND ART

Strong mid-infrared (mid-IR) and far-infrared (THz) spectral absorption, arising from fundamental rotational-vibrational modes of materials, has long been used as their unique molecular signature. Mid-IR and THz absorption also promises exceptional contrast in imaging, providing exciting applications from, for example, tissue, polymeric, geological, and forensic samples. Currently, Fourier Transform Infrared (FTIR) spectroscopy and Attenuated Total Reflection (ATR) spectroscopy are the most widely used methods to measure and image mid-IR and THz absorption. Despite nearly 70 years of microscopy developments, however, IR imaging significantly lags optical microscopy in instrumentation capabilities and use. Most common detector materials are non-responsive over the IR spectral bandwidth (free-space wavelength range 2-25 µm) and THz spectral bandwidth (25-1000 µm) and glass absorbs strongly (for wavelengths longer than about 5 µm), making light microscopy optics unusable. In contrast to other chemical imaging approaches, hence, mid-IR/THz imaging remains expensive due to the need for specialized sources and detectors, challenging design for the large spectral bandwidths, and need for specialized experimental setups. More importantly, the lack of integration between IR/THz imaging and optical imaging prevents the realization of synergy between the two for transformative applications. One example is augmenting and automation of histopathology based on IR imaging combined with machine learning.

No current imaging techniques are capable of rendering spectral information derived from infrared (IR) or terahertz (THz) excitation of molecules at spatial resolution exceeding that governed by the wavelength of the exciting radiation and at the large field of view of optical microscopy on the 100s of $\mu m^2$ to $cm^2$ scale. Thus, cellular identification and their transformations across a large sample that is typical for biomedical analyses on the basis of known photothermal techniques is impossible.

SUMMARY OF THE EMBODIMENTS

The deficiencies of the prior art are overcome by providing a hybrid infrared-optical (IR-OH) approach that overcomes the extant limitations of IR/THz imaging and considerably extends the contrast for optical microscopy. The embodiments disclosed herein exploit phase-sensitive optical imaging to measure IR/THz absorption by detecting the photothermal response in a sample introduced by a IR/THz heating beam.

In accordance with embodiments of the invention, methods and apparatus are provided for imaging a response of a sample to radiative heating. A method in accordance with one embodiment has steps of:

illuminating a first area of the sample with a radiative heating beam;

illuminating a portion of the first area with a probe beam;

collecting light exiting the sample due to interaction of the probe beam with the sample;

superimposing the light exiting the sample with a reference beam derived from the probe beam, wherein the reference is characterized by an optical phase relative to the probe beam;

detecting a spatial portion of the light exiting the sample and the reference beam with at least one detector to generate an interference signal; and processing the interference signal to obtain an image of the sample associated with absorption of the radiative heating beam.

In accordance with other embodiments, the detector may encompass a camera with multiple detectors. The reference beam may, or may not, traverse a portion of the sample within the scope of the invention.

Interaction of the probe beam with the sample may include at least one of scattering, reflection and transmission of the probe beam. The radiative heating beam may be characterized by a wavelength at least as long as the mid-infrared, and may be temporally swept in frequency to obtain a spectrum. The radiative heating beam may be provided as a free-space propagating wave or a propagating mode in a waveguide. Further, the radiative heating beam may be provided as an evanescent wave formed by total internal reflection in a suitable crystal or as an evanescent field formed by a propagating mode in a waveguide, on which the sample is located.

In accordance with other embodiments of the present invention, illuminating a first area of the sample with a radiative heating beam may include modulating the radiative heating beam at least one of temporally and spatially.

The probe beam may be characterized by a wavelength shortward of 3 µm. Illuminating a portion of the first area with a probe beam may include focusing the probe beam to a focus, and detecting a portion of the first area with a probe beam may include focusing a reflected or scattered beam to a focus on either a single detector or a camera. The portion of the first area illuminated with a probe beam may be a contiguous portion, or may include multi-focal point sub-portions.

In accordance with further embodiments of the present invention, the portion of the first area illuminated with a probe beam may be varied as a function of time, such as by translating a focus of the probe beam in such a manner as to vary the portion of the first area illuminated as a function of time. The detected spatial portion of the light may also be varied as a function of time.

In yet further embodiments, the heating beam may be modulated in time, and, more particularly, it may be modulated in time at a rate exceeding a camera frame rate of the camera, where a camera is employed. The probe beam may be monochromatic, polychromatic at discrete wavelengths or it may be of low coherence, as defined below. A first area of the sample may be illuminated by the heating beam and the portion of the first area of the sample may be illuminated by the probe beam, both via optics that are common at least in part.

In other embodiments of the current invention, light exiting the sample may be coupled toward a detector via optics that are common at least in part with optics, such as a microscope objective, through which the portion of the first area of the sample is illuminated.

In still other embodiments, at least one of a specified phase shift and frequency shift may be imposed on the reference beam as a function of time, such as by imposing a path length difference in a path traversed by the reference beam relative to the light exiting the sample. Additionally, a cell type may be identified, in accordance with some embodiments of the invention, on the basis of a measured molecular-specific response of the sample to radiative heating.

In accordance with another aspect of the present invention, an apparatus is provided for wide-field photothermal measurements of a sample. The apparatus has a first source for generating a radiative heating beam at a wavelength longer than 2.5 μm and a second source for generating a probe beam at a wavelength shorter than 3 μm, and optical arrangements for focusing both beams of at least partially overlapping areas of the sample. The apparatus also has an interferometer for superimposing light exiting the sample with a reference beam derived from the probe beam, a detector for detecting a spatial portion of the light exiting the sample and the reference beam to generate an interference signal and a processor for the interference signal to obtain an image of the sample associated with absorption of the radiative heating beam.

In accordance with other embodiments of the present invention the apparatus may also have a phase shifter for imposing a phase shift between the reference beam and the probe beam. More particularly, the phase shift may correspond to a path length difference imposed between the reference beam and the probe beam. The second source may be a monochromatic source as one chosen from a group of monochromatic sources including gas lasers and laser diodes. The second source may also be a low-coherence source, such as one chosen from a group of low-coherence sources including superluminescent diodes, light-emitting diodes, supercontinuum lasers and picosecond lasers. Moreover, the interferometer may be chosen from a group of interferometer configurations including Michelson, Mach-Zehnder, Mirau and Linnik interferometers. Data may be analyzed according to optical coherence tomography principle, where low-coherence interferometry is exploited to obtain depth-resolved images of the sample associated with the absorption of the radiative heating beam.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which.

DETAILED DESCRIPTION OF SPECIFIC EMBODIMENTS

Definitions

Figure 1:
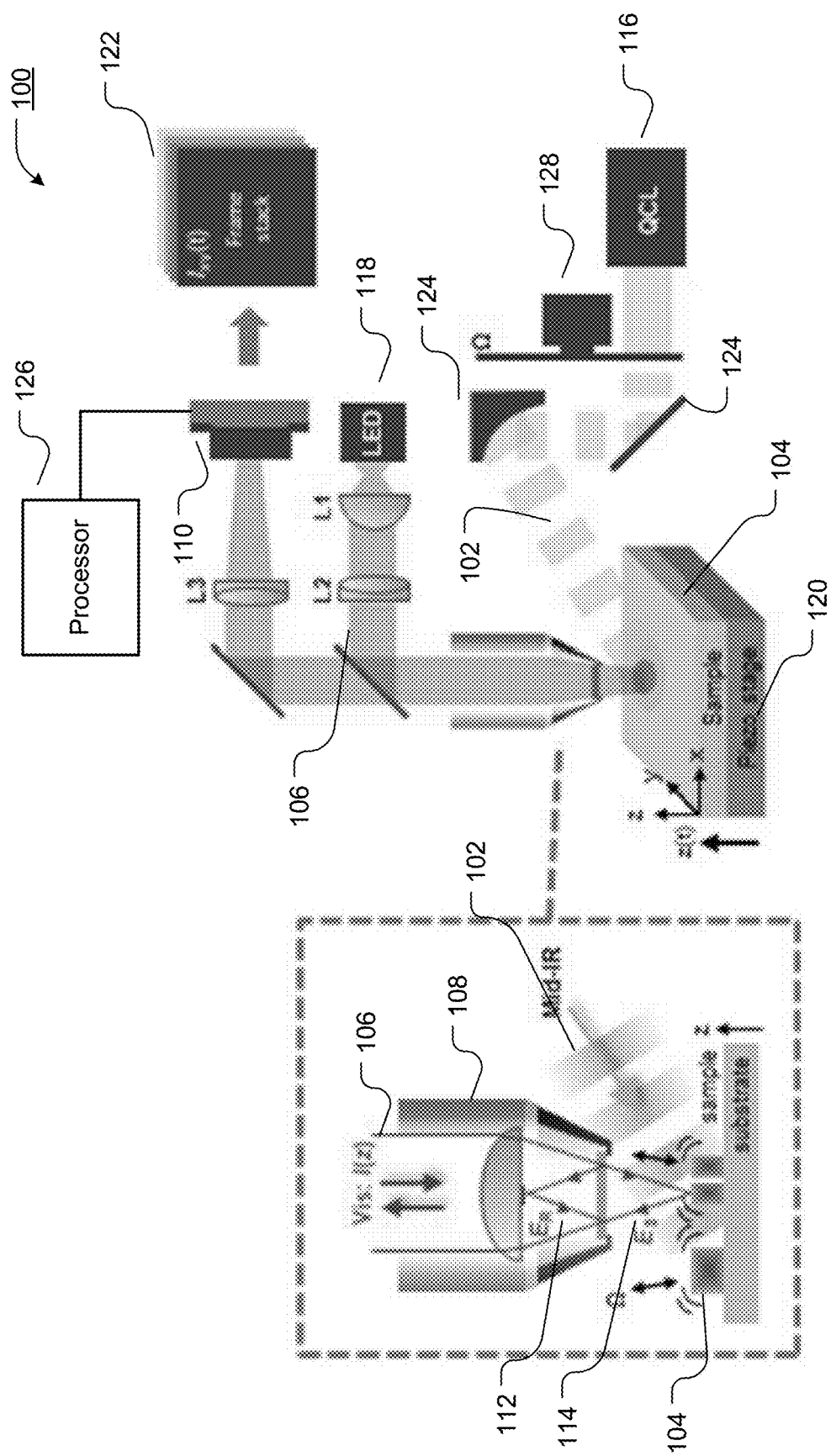
FIG. 1 depicts an infrared-optical hybrid imaging apparatus in accordance with an embodiment of the present invention.

As used in this description and the accompanying claims, the following terms shall have the meanings indicated. Unless defined or otherwise required by context, all technical and scientific terms used herein have the same meaning as commonly understood by one of skill in the art to which the invention pertains.

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, or photothermal temperature rise, constitutes an image. So, also, does an array of numbers, such as a 3D holographic dataset, in a computer memory or holographic medium. Similarly, "imaging" refers to the rendering of a stated physical characteristic in terms of one or more images.

The terms "object," "sample," and "specimen" shall refer, interchangeably, to a tangible, non-transitory physical object capable of being rendered as an image.

The term "mid-infrared" as used herein refers to wavelengths between 2.5 μm and 12 μm.

The term terahertz (THz) radiation as used herein refers to radiation at frequencies between 300 GHz and 30 THz, or, equivalently, at wavelengths between 1 mm and 10 μm. The term "far infrared" shall be defined as synonymous with "terahertz" for purposes of the present description. This range subsumes many molecular rotational transitions, and when a rotational frequency lies at a longer wavelength, it shall be referred to herein as a radio frequency transition.

The term radio frequency (rf) radiation, as used herein, is defined to refer to radiation at any frequency lower than 300 GHz or, equivalently, longward of 1 mm.

The term "camera," as used herein and in any appended claims shall denote an array of photodetector elements together with any associated optics and/or electronics.

A full well capacity of a camera, whether CMOS or CCD, shall be denoted herein as a "high" full well capacity if and only if it exceeds 100,000 electrons. Cameras characterized by high full well capacity find applications in background-noise-limited astronomy, for example. The combination of high full well capacity (as defined) with high frame rate (defined as greater than 100 Hz) has not been suggested in a bioimaging context.

An electromagnetic beam shall be denoted herein as being of "low coherence," whether due to the nature of its source or to subsequent actions taken to cause its decoherence, if and only if the coherence length of the beam is shorter than 300 μm, and/or the spectral width $\Delta k/k\_0$ is at least 1%, with k_0 denoting the central wavenumber of the spectrum illuminating the sample, while Δk denotes the range of illuminating wavenumbers. Conversely, an electromagnetic beam shall be denoted herein as being of "monochromatic" if the coherence length is longer than 300 μm, and/or the spectral width Δk/k_0 is less than 1%. It is to be understood that, within the scope of the present invention, the wavelength of the source need not be fixed in time, indeed, the wavelength of the source may be swept in time.

A reference beam derived from a first electromagnetic beam may be characterized at a specified point in space and time by an optical phase relative to that first electromagnetic beam, and that optical phase, most generally, may also be a function of frequency, ϕ(r,t,k). That "optical phase" may be said, herein, without loss of generality, to characterize the reference beam.

The term "phase shifter" shall refer to any modality currently known or later discovered for imposing a phase shift upon an electromagnetic beam relative to a fiducial reference. The choice of a phase shifter to be employed in a specified application is a matter of design choice within the ken of a person of ordinary skill in the art.

The term "optical arrangement" refers to any elements employed within the optical or radio arts for coupling a beam from one locus to another. It may include, without limitation, any combination of transmissive or reflective optics or both, and may also include free-space propagation. The design of an optical arrangement to meet specified design objectives is considered to lie within the ken of a person of ordinary skill in the art. The inventors do not intend to have this limitation interpreted as a means plus function under 35U.S.C. 112(f).

The word "portion" as used herein and in any appended claims shall encompass any non-zero fraction, up to and including the entirety.

The term "phase" as used herein and in any appended claims shall refer to the optical phase, e.g. the phase of a probe beam relative to a reference beam, unless further specified. Any reference to the phase of an electronic signal shall be made explicitly.

The embodiments disclosed herein are directed at obtaining measurements of a photothermal response indicative of IR/THz absorption in a sample. For this purpose, one heating beam (mid-IR, THz) is used to induce a photothermal response in the sample and one probe beam (in the light spectrum visible to humans, ultraviolet or near-infrared spectral range) is used to sense this response. This provides the following advantages over regular IR imaging: (a) the spatial resolution is mainly determined by the probe beam and thus can be made to be better than the diffraction-limited resolution of regular IR imaging; (b) superior optical components (such as microscope objectives) and detectors (such as CMOS cameras) can be employed to measure IR/THz absorption, affording better image correction, pixel count and sensitivity, while IR/THz needs specialized optics and detectors that are inferior and costly in comparison to their optical counterparts; and (c) the technique disclosed herein provides an opportunity to suppress IR/THz scattering contributions, hence more reliable IR/THz absorption measurements can be obtained.

FIG. 1 depicts an infrared-optical hybrid imaging apparatus 100 in accordance with an embodiment of the present invention. A heating beam 102 with a wavelength at least as long as the mid-IR (i.e., longer than 2.5 μm) illuminates an area of a sample 104 and induces a photothermal response across the sample 104. To probe the photothermal response, a probe beam 106 with a wave length in the ultraviolet, visible or near-infrared spectrum (i.e., shorter than 2.5 μm) illuminates at least part of the area that is illuminated by the heating beam 102. The area illuminated by the probe beam 106 may be a contiguous portion, or it may include multi-focal point sub-portions that may vary over time, as described further below. It is also expressly contemplated that the area illuminated by the probe beam 106 may vary as a function of time, either through adjusting the optics that guide the probe beam onto the sample or by moving the sample. Varying the area illuminated by the probe beam 106 results in varying the area captured by the detector 110. As shown in FIG. 1, the heating beam 102 and probe beam 106 may use separate optics, such as objective 108 for the probe beam and optics 124 for the heating beam. However, the heating beam 102 and probe beam 106 may also partially share the same optics.

The probe beam 106 is scattered, reflected at the sample 104 as reflected probe beam 114, or transmitted through the sample 104. An objective 108 collects the probe beam from the sample and, together with additional optical components (not shown), an image of the sample is formed on a camera 110 that is sensitive to the probe beam. A reference beam 112, generated from the illuminating probe beam 106, is superposed with the reflected probe beam 114 from the sample 104 at the camera 110 to implement interferometric detection. While the reference beam 112 is shown separated from the sample, it is expressly contemplated that the reference beam may traverse a portion of the sample 104. The probe beam 106 and reflected probe beam 114 may partially share the same optics, such as objective 108. However, the probe beam 106 and reflected probe beam 114 may also use separate optics.

The reference beam 112 is temporally (e.g. phase shift or modulation of optical path length) or spatially modulated (e.g. nonzero angle of incidence akin to off-axis holography) relative to the probe beam 106 to resolve the phase of the reflected probe beam 114 from the sample 104. The heating beam 102 may be temporally swept in frequency to obtain a spectrum, or it may be modulated. Temporal or spatial modulation of the heating beam 102 introduces a modulation in the photothermal response in the sample, for example at frequency Ω. This in turn modulates the phase of the reflected probe beam 114 from the sample, as for example caused by vibration of the sample surface at frequency Ω and a subsequent modulation of the optical path length of the probe beam 114 that is reflected at the sample surface. To record the photothermal response of the sample 104, one or more camera frames are recorded and processed on a processor or computer 126. Importantly, by using a camera, thousands to millions of locations on the sample can be probed simultaneously.

The sample 104 may be heated with a monochromatic mid-IR laser beam from a quantum cascade laser 116 (QCL, for example MIRcat, available from Daylight solutions, San Diego, Calif.) that can be tuned to molecular vibration bands in the sample. The mid-IR beam 102 is intensity-modulated with an optical chopper 128 at frequency Ω (the chopper may, for example, be an MC2000B, available from Thorlabs, Newton, N.J.) and directed at the sample 104 for illumination from the side. Beam direction and shaping may be done with respective optics 124, such as concave and parabolic mirrors, to produce a nearly circularly shaped illumination field on the sample 104. To probe the sample deformation induced by the mid-IR beam, wide-field interference microscopy is applied. Exemplarily, the sample 104 is illuminated with light from a narrow-band LED 118 emitting at a nominal λ_0=660 nm and 20 nm spectral bandwidth (such LED may, for example, be an M660L4, available from Thorlabs, Newton, N.J.). The LED is strobed in synchronization with the beginning of each camera frame for a time of ~500 μs. The reflected light 114 from the sample is collected with an interference objective 108. The interference objective 108, or interferometer, may be a Michelson, Mach-Zehnder, Linnik, or Mirau interferometer. Exemplarily, in a Mirau interferometer, such as a 50× CF IC Epi Plan D1 (available from Nikon, Melville, N.Y.), the reflected light 114 is interfered with the reference beam 112 for phase detection. To scan the delay $\tau$ between sample and reference beam, the sample can be translated vertically (z) by a linear piezo stage 120 (such as a P-611.3, available from Physik Instrumente, Auburn, Mass.). While the sample 104 is translated by the piezo stage 120 at constant velocity z(t)=vt, a sequence of interferometric images is registered with a detector 110, such as a monochromatic camera, at a high frame rate F=500 Hz, yielding interferograms 122 for each pixel (x,y) at each z position. It may be necessary to focus a reflected or scattered beam to focus on a single detector 110, such as the camera. The interferograms 122 are demodulated on a processor 126, such as a computer, at frequencies S and $\Omega$–S, where S is the fringe frequency introduced by the vertical translation of the sample. Note that for frequencies $\Omega$>F, demodulation is performed at frequencies S and $\Omega'$–S where $\Omega'$ is the low frequency alias of $\Omega$ relative to F. The IR absorption image is obtained by dividing $\Omega$–S by S data sets pixel by pixel.

Improvement in Sensitivity by Using a High Full Well Capacity Camera

The relative change in intensity of the collected probe beam 114 owing to a photothermal response of the sample 104 is a weak effect and can be expected to be in the range of 1:100 to 1:10,000. Thus, the signal-to-noise ratio (SNR) in the detection of the probe beam needs to be maximized in order to obtain sufficient sensitivity in measuring a photothermal response in the sample. Wide-field implementations of photothermal imaging need cameras. However, cameras are usually considered to have an inferior SNR performance in comparison to photo detectors. The SNR limiting factor imposed by the camera is the full well capacity of the camera sensor that defines the amount of charges an individual pixel can hold before saturation. Typical camera sensors exhibit a full well capacity of the order of 10,000 electrons, and SNR is typically in the range of 100:1, and thus far from the needed SNR for ensuring high sensitivity in a photothermal measurement.

One embodiment of the invention disclosed herein employs a camera with high full well capacity to improve SNR performance. One example of such a camera is commercially available from Adimec Electronic Imaging Inc, Woburn, Mass. By offering two million electron full well capacity it increases SNR to 1400:1 and is thus in the range of the expected photothermal-induced modulation depth of the probe beam. Alternatively, SNR performance may be improved by increasing the frame rate of the camera. Regular camera technology offers frame rates in the 10s of Hz to low 100s of Hz (e.g. cameras sold by Thorlabs, Newton, N.J., or Point Grey, Vancouver, BC, Canada). High speed cameras with frame rates in the 10s of kHz with some models operating up to MHz frame rates are commercially available, for example the Photron Fastcam SA-X2 (Photron USA, San Diego, Calif.) or the Phantom v2640 (Vision Research, Wayne, N.J.). Therefore, another embodiment of the invention disclosed herein employs a camera where the high frame rate enables the collection of a large number of electrons per pixel and second before saturation occurs. This allows high SNR even in the case of only moderate full well capacity.

Strobed Probe Beam for Photothermal Imaging at Modulation Rates $\Omega$ of the Heating Beam Greater than the Camera Frame Rate at Only Little Penalty in SNR Prior art describes the use of cameras with short exposure times to resolve the photothermal response of the sample at high modulation rates $\Omega$ of the heating beam. If combined with standard light sources such as HeNe lasers or LEDs, the prior art devices may yield reduced SNR owing to the fact that the camera collects photons only for a brief amount of time (during exposure), while most of the photons are lost while the camera downloads the frame from the sensor.

In some embodiments disclosed herein, a strobed probe beam is employed in combination with long camera exposure times (of the order of or greater than $1/\Omega$). In one embodiment, intensity modulation of the probe beam is introduced at a frequency related to the modulation rate $\Omega$ of the heating beam. The short, periodic sample illumination by the probe beam "freezes" the photothermal response in the sample. Exemplarily, the intensity modulation signal of the probe beam has a fixed phase angle (electronic phase) to the heating beam modulation signal. For each recorded frame, the camera then integrates the detected probe beam over at least a period length of $1/\Omega$. This significantly increases the SNR of the probe beam as the camera exposure time can be set very close to the period of frame rate 1/F, and most of the photons emitted by the light source are collected by the camera. Most importantly, cameras with slow frame rates F can be employed in combination with fast modulation of the heating beam at rates $\Omega$>>F. This allows using simple camera technology in lieu of special high-speed camera technology.

For example, the heating beam is intensity modulated at a frequency $\Omega$=1100 Hz, while the camera only runs at a frame rate of F=500 Hz. By strobing the LED with a burst of two pulses at a repetition rate of 1100 Hz and at a duty cycle of 30%, where the burst is triggered with each camera frame, an aliased signal of the photothermal response of the sample can be obtained at $\Omega'$=100 Hz, the amplitude of which is much larger than that of a continuous probe illumination. Note that the probe beam can be modulated with a rectangular waveform at a single frequency, or more generally, with any intensity waveform (e.g. a sine wave). Alternatively, laser sources might be employed that intrinsically provide a pulsed lasing operation.

In another embodiment, the reference beam is frequency-shifted with a frequency relative to the probe beam and at a rate relative to the heating beam modulation rate $\Omega$. This yields a low frequency beating of the probe beam from the sample against the reference field that can be conveniently recorded by the camera at a much lower frame rate F<<$\Omega$. In this case, the probe beam could also be a continuous wave (i.e., not pulsed).

Introducing Low Coherence in the Probe Beam to Reduce Unwanted Coherence Artifacts in the Photothermal Data Prior art does generally not discuss the role of the coherence of the probe beam. Some authors have pointed out that superluminescent diodes (SLDs) can be advantageous as they have a relative short coherence length in comparison to conventional lasers and help to reduce the detection of unwanted scattered light and hence yield more reliable photothermal measurements. However, the role of the coherence length of the probe beam in widefield imaging has not been addressed. It is known that the spatial and/or temporal coherence in widefield interferometric imaging can reduce the image quality owing to speckle or residual reflections with other surfaces in the optical setup.

In some of the embodiments disclosed herein, light sources of low spatial and/or temporal coherence are used to generate the probe beam in order to reduce unwanted interference artifacts in the photothermal measurements (e.g. less speckle artifacts). In one embodiment, the temporal coherence is limited to a length scale that corresponds to the distance between optical surfaces in the microscope setup to avoid unwanted interferences (e.g. millimeter-scale for typical objectives). Further reduction of the temporal coherence provides depth gating as it is typically exploited in low coherence microscopy. This could avoid unwanted interferences between different layers in the sample (e.g. substrate and the sample surface). This could also provide additional topography information on the sample. For example, typical LED light sources are narrowband sources (such as the M660L4, available from Thorlabs, Newton, N.J., having a center wavelength of 660 nm with 20 nm bandwidth) and provide a depth resolution on the scale of 10 micrometers. Other examples of low coherence light sources are superluminescent diodes (SLDs), supercontinuum lasers, and picosecond lasers.

In another embodiment, spatial coherence is reduced for example by using incoherent light sources such as an LED, or by using a coherent light source in combination with a rotating diffuser plate. Alternatively, swept sources might be used to generate the probe beam where the frequency sweeping of the source provides a means to reduce interference artifacts and to obtain depth information, as it is the case in swept-source optical coherence tomography.

In another embodiment, the low spatial and/or temporal coherence of the probe beam is exploited to generate depth-resolved images of the photothermal response in the sample akin to the optical coherence tomography principle. The temporal coherence of the light source provides depth gating of the photothermal response in the sample. In one embodiment, a wide-field arrangement (FIG. 1) is combined with a broadband light sources such as LED with white color emission or a Tungsten light bulb, effectively implementing full field coherence optical tomography (FFOCT). In another embodiment, a confocal arrangement (FIG. 3) is combined with low coherence light sources such as SLDs and an optical spectrometer, effectively implementing spectral-domain optical coherence tomography (SD-OCT). In another embodiment, a confocal arrangement (FIG. 3) is combined with a frequency-tunable monochromatic light source to implement swept source optical coherence tomography (SS-OCT) with infrared excitation.

Temporal or Spatial Modulation of the Phase or Optical Path Length of the Reference Beam Relative to the Probe Beam Prior art has described the possibility of measuring the photothermal response by implementing an interferometric detection to measure amplitude and phase of the probe beam from the sample. However, it was not described how amplitude and phase information from the probe beam is extracted. Generally, an interferometer yields a static measurement where amplitude and phase of the probe beam are not determined directly, but rather a value proportional to the amplitude A times the cosine of the phase phi is obtained: detected signal ~A*cos (phi). Here, phi is the phase difference between the probe beam and the reference beam. Importantly, this measurement is highly influenced by changes in the optical path length between the two beams, as caused by instabilities and drifts of the interferometer or by sample topography. As a result, such an interferometric measurement is unreliable In one embodiment of the invention disclosed herein, a temporal modulation of the reference beam relative to the probe beam is introduced. For example, a linear-in-time phase shift can be introduced in the reference beam with a suitable device, e.g. by reflection of the reference beam from a piezo-controlled mirror, by acousto-optical devices, or by spatial light modulators. Such an arrangement is also called heterodyne interferometry. This modulation is performed simultaneously to the operation of the proposed device, i.e. simultaneous to the illumination of the sample with a heating beam modulated at frequency $\Omega$. A series of measurements of the probe beam is made to capture a significant length of the temporal modulation that allows for accurately determining amplitude and phase of the probe beam. In case of a linear-in-time phase shift, recording of a few modulation periods will yield a signal that can be analyzed by Fourier Transform (FT). In the FT, a carrier signal at frequency S can be detected that corresponds to the frequency of the phase modulation. The photothermal response would then appear as additional peaks at frequencies $S-\Omega$ and $S+\Omega$.

Figure 2:
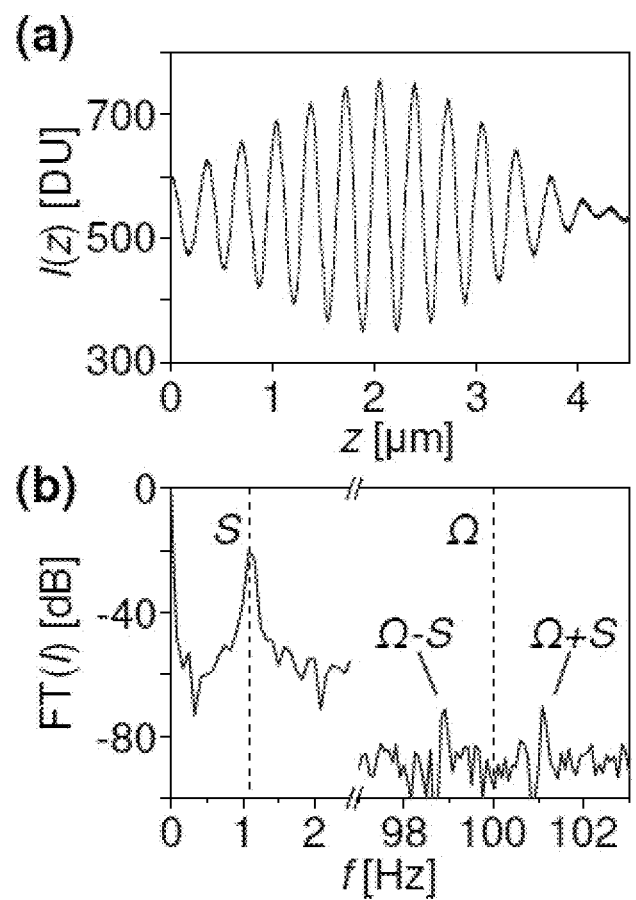
FIG. 2 shows results of interferometric measurement of the photothermal response.

FIG. 2 shows the results of interferometric measurement of the photothermal response in the sample introduced by a heating beam that is intensity-modulated at frequency $\Omega$. FIG. 2 (a) depicts the detected change in intensity of the collected probe from the sample at a specific position on the sample while the sample is translated vertically by the piezo stage. FIG. 2 (b) shows the Fourier transform of FIG. 2 (a), revealing the fringe frequency S and two additional peaks at frequencies $S-\Omega$ and $S+\Omega$. Demodulation at $S-\Omega$ or $S+\Omega$ retrieves a signal that is a measure of the photothermal response in the sample. Simultaneous demodulation at more than one frequency might be applied to improve signal-to-noise ratio of the photothermal signal, or to separate signal contributions from surface expansion and reflectivity changes, e.g. by analysis of the electronic phase of the demodulated signals.

In another embodiment, the reference beam is frequency-shifted relative to the probe beam, wherein the frequency offset is M. According to the heterodyne interferometry principle, demodulation at the sum of frequencies, e.g. $M+\Omega$, yields amplitude and phase of the photothermal signal in the probe beam from the sample. Such frequency shift may be accomplished by using acousto-optical frequency shifters. Two shifters may be employed to generate a frequency M that is of the order of the camera frame rate F, e.g. $M=F/4$ to implement the equivalent of phase shifting interferometry.

The embodiment described above can easily be extended to a non-monochromatic probe beam such as a probe beam exhibiting a number of discrete frequencies (e.g. several laser lines), a narrowband probe beam (e.g. as emitted by an LED) or a broadband probe beam (e.g. a white light source). In this case, a temporal modulation of the reference beam relative to the illuminating probe beam can be understood as a phase modulation of each of the individual frequencies or frequency bands in approximation, or as a modulation of the optical path length of the reference beam relative to the probe beam. For example, all of these types of modulation can be produced by reflecting the reference beam from a moving mirror.

In another embodiment, a spatial modulation of the reference beam relative to the probe beam is introduced. Such spatial modulation may be produced by choosing different angles of incidence on the camera of the reference beam and the probe beam, effectively implementing an off-axis holography arrangement. In this case, the different angles of incidence produce a spatially varying phase shift between the reference beam and the probe beam. In case of a monochromatic beam, reflection of the probe or reference beam at an angled mirror may produce the difference in angles between the probe beam and the reference beam. In case of a non-monochromatic beam, transmission or reflection of the probe or reference beam at a grating may produce the difference in angles between the probe beam and the reference beam.

Alternatively, a grid of polarizers might be used to create a specific pattern of phase shifts between the reference beam and the probe beam. For example, camera sensors are commercially available where each individual pixel has its own polarizing filter in an arrangement that a 2×2 pixel block includes polarizer angles of 0, 45, 90 and 135 degrees (one example is the camera sensor of the Sony IMX250MZR, available from Sony Corporation of America, New York, N.Y.). In combination with suitable polarization of the reference beam and probe beam (e.g. left- and right-handed circularly polarized, respectively), a spatial modulation of the phase difference between the reference and the probe beam is created across the camera sensor that allows for determining amplitude and phase of the probe beam.

In another embodiment, the reference beam is used to provide interferometric amplification of the probe beam. This could be useful to detect a modulation in surface reflectivity at frequency $\Omega$, caused by absorption-induced changes of the refractive index, with higher sensitivity. Analog to the description above in reference to FIG. 2, signal demodulation at S−$\Omega$ or S+$\Omega$, for example, would be performed to extract the modulation signal.

Side Illumination of the Heating Beam

Most prior art describes a dual beam experiment where heating and probe beam are focused on the sample by a single objective. Because for the desired application of the embodiments disclosed herein, the heating beam is at mid-IR or THz frequencies but the probe beam is at UV/visible/near-IR frequencies, the choice of the available objectives is limited. Reflective objectives are typically employed as they do not show chromatic aberration, however, the low numerical aperture (NA) in the range of 0.3 to 0.6 and central obstruction yield an inferior image quality in comparison to optimized objectives for visible frequencies (with NA up to 1.4). Further, most point-scanning modalities of photothermal imaging focus the heating beam to a small spot in order to increase SNR, while wide-field imaging requires illumination of an area of the sample, the latter does not necessarily need an objective to do so and thus exhibits relaxed requirements to the needed optics.

Disclosed herein is a design where an objective is used to collect the probe beam from the sample while the heating beam is incident from a different angle. For example, the objective is positioned perpendicular to the sample while the heating beam is incident from the side, as shown in FIG. 1. In the simplest case, the heating beam is a collimated beam from a laser that is directed at the sample. Further, the beam diameter may be increased or decreased with additional optics such as a beam expander, again yielding a collimated beam. Additionally, a single optical component such as a lens or a parabolic mirror may be used to produce a convergent beam where the sample would be located between the focal point and the optical component to ensure area illumination. Side illumination can be accommodated even when relatively high-NA objectives are employed to collect the probe beam from the sample. Additional optics may be used to compensate for elongation of the illuminated area by the heating beam for oblique angles of incidence. Objective and side illumination can be located on the same side of the sample, thus enabling photothermal measurements on thick samples or strongly absorbing samples where illumination from the other side than the objective may not be feasible. In another design, the probe beam illuminates the sample from one plane and is collected from the opposed plane of the sample in a transmission geometry. In this case, the heating beam is incident from the side on either of the planes.

Power Normalization of the Heating Beam

Sources for generating the heating beam, such as gas lasers or quantum cascade lasers, typically do not provide for a means to generate a beam at a set power level. In regular IR/THz measurements, a power normalization can be provided by taking a reference measurement e.g. on an empty location on a sample. In contrast, such reference measurement is difficult to do intrinsically, as the absence of absorbing material yields a zero photothermal signal in principle. A reference area might be provided on the sample as it is the case in near-field microscopy, but this might be cumbersome.

In one embodiment of the invention disclosed herein, a power sensor measures the power of the heating beam to provide a means to normalize the photothermal signal. Such power measurement may be provided in real time by sampling a portion of the heating beam. Such power measurement may also be provided before or after photothermal data acquisition, by e.g. redirecting the heating beam momentarily to the power sensor with a motorized flip mirror.

Real-Time Data Processing

Recording of the photothermal signal is expected to yield a large bandwidth of data that needs to be processed in real time. The minimum frame rate of the camera is twice the fringe frequency S. It is, however, advantageous to record data at even higher frame rates to resolve vibrations in the optical setup and thus improve SNR of the photothermal signal. This, together with megapixel frame sizes, yields large amounts of data that need to be processed in real time.

In some of the embodiments disclosed herein, data is streamed from the camera to a data processing device (e.g. a computer or field programmable gate array FPGA). Signal demodulation is implemented in software using, e.g., discrete Fourier transform or fast Fourier transforms. A computer is used to demodulate at one or more frequencies in real time at data rates of, for example, 10 Megabytes/s, 100 Megabytes/s, 1 Gigabyte/s, 2 Gigabytes/s as streamed from the camera via an interface, for example via CoaXPress. Only the result of the demodulation may be stored, thus greatly reducing data volume. Such data processing might be performed on an FPGA that may directly interface the camera sensor. In this case, the data volume refers to the data transferred from the sensor to the FPGA. For example, acquiring data over 6 seconds at a camera frame rate of 500 Hz yields 3000 frames. Demodulation at two frequencies reduces data volume to $\frac{1}{1500}$. Real-time data processing is essential for acquiring photothermal data over large areas.

Confocal Arrangement/Point Scanning

Figure 3:
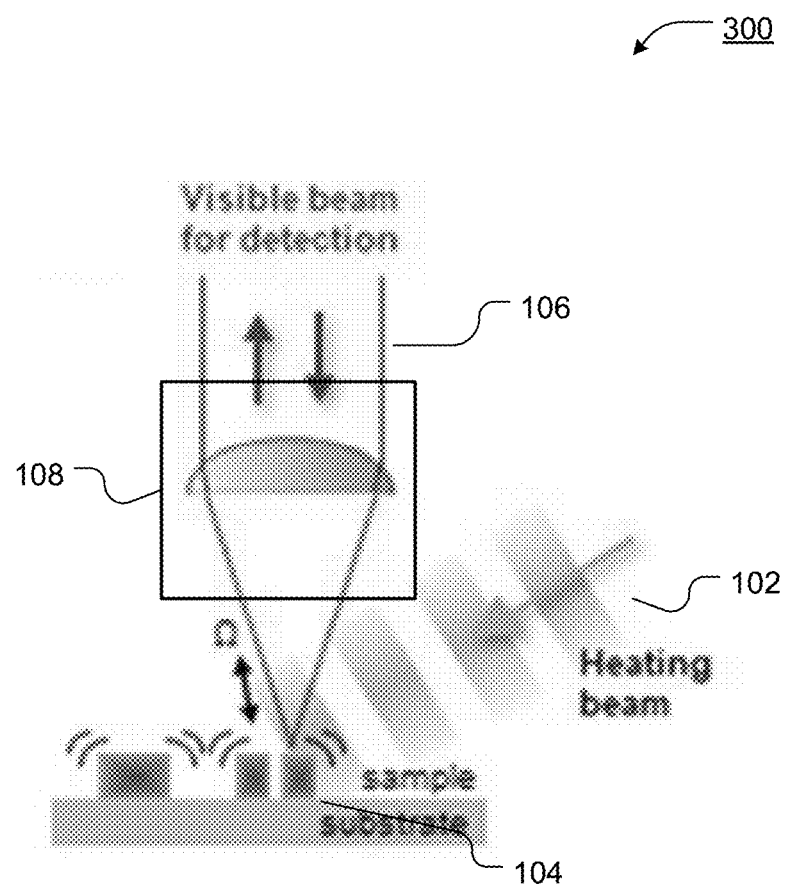
FIG. 3 depicts an infrared-optical hybrid imaging apparatus in accordance with another embodiment of the present invention.

FIG. 3 depicts an infrared-optical hybrid imaging apparatus 300 in accordance with another embodiment of the present invention. The probe beam 106 is focused to one or more locations on the sample 104. A single focus can be obtained by simple focusing of a laser beam according to the classic confocal principle. Multiple foci may be obtained by producing a number of beamlets from a laser beam by using a grating or an acousto-optical modulator, for example, and subsequent focusing of all beamlets by an objective. The probe beam interacts with the sample as described above in reference to FIG. 1. The scattered field is collected from the sample with an objective 108, forming one or more beamlets. Each of these beamlets is superposed with a reference field, as described above in reference to FIG. 1, and detected by a photodetector or an array of photodetectors (not shown). To implement a phase measurement of the probe beam from the sample, the reference beam is temporally modulated relative to the illuminating probe beam by, for example, using a phaseshifting or frequency shifting approach as described above. Demodulation of the detector signal or the signals from an array detector with for example a lock-in amplifier yields the photothermal response from the locations on the sample that are illuminated by the probe beam. The confocal arrangement allows for concentrating more photons of the probe per sample area, thus yielding an improved sensitivity in comparison to the wide-field modality described above that distributes the probe beam over a large area.

The temporal modulation of the phase or optical path length of the reference beam relative to the probe beam may be fast such as in phase-shifting interferometry where the reference beam is phase-shifted relative to the probe beam by at least $2\pi$ during the pixel dwell time. Alternatively, the temporal modulation may be slow such as in synthetic optical holography, where the phase shift between reference and probe beam is quasi constant during the pixel dwell time. In the latter case, demodulation at frequency $\Omega$ may be applied first at each pixel, forming a demodulated hologram image, which is then reconstructed with spatial filtering in Fourier space to yield an amplitude and phase image indicative of the photothermal signal across the imaged area.

Side illumination of the heating beam is a particularly favorable implementation for sample scanning modalities of point scanning-based imaging. In this case, a relatively tight focus of the heating beam may be achieved with simple optical elements, such as a lens or a parabolic mirror. The position of this focus would be fixed relative to the focal plane of the objective used to collect the probe beam from the sample. Scanning the sample while recording the data would then yield a photothermal image of the sample.

Side illumination may also allow for effective implementation of beam scanning modalities of point scanning-based imaging. In this case, the heating beam may be scanned to move the focus across an area of the sample with a suitable device, e.g. a galvanometer-based scanner as commonly found in confocal microscopes. Synchronizing the scanning of the heating beam with the scanning of the probe beam could allow for rapid acquisition of a photothermal image of the sample.

In addition to sequentially recording the photothermal response of the sample using a single focus, an image of the sample can be formed by translation of the focus/foci across the sample while recording the detector data. Generally, large areas of the sample can be imaged by first acquiring individual images at different positions on the sample and then combining them to produce a single image. For practical reasons, automatic focus finding might be needed to image very large areas. This could be achieved by taking advantage of the low-coherence source. By either measuring a spot on an empty space on the sample, or on the sample itself, a vertical scan can be executed to find the maximum fringe contrast, which would indicate the location of the sample surface. Alternatively, non-interferometric focusing algorithms could be applied that seek to maximize image contrast, spatial frequency content, or some other appropriate metric.

Multi-Foci Point-Scanning for Rapid Image Acquisition

Prior art mostly describes point scanning modalities where a single focus is employed to read out the photothermal response of the sample. This results in slow imaging speeds. In some of the embodiments disclosed herein, a plurality of foci is employed to simultaneously measure the photothermal response at different loci at the sample. In one embodiment, an array of beamlets is produced from the source generating the probe beam by means of acousto-optical devices, including acousto-optical frequency shifters, modulators and deflectors. This array of beams is then focused on the sample and collected from the sample as described previously with the case of a single probe beam. The probe beamlets are then detected with an array detector, where the signal of each detector is processed individually to extract the photothermal signal. The so-obtained photothermal signal can then be assigned to a location on the sample by the known relationship between the position of the respective element of the array detector and the position on the sample.

Alternatively, each beamlet may be encoded with a designated intensity modulation or a designated frequency shift, and then a single detector may be employed to register all beamlets simultaneously. Data processing, such as demodulation, extracts the photothermal signal for each of the loci on the sample. For example, beamlet number n (n is an integer number) may be frequency shifted by nM (M is a frequency) and focused on the sample position (nX+X0,Y0), where X is the step between the individual foci aligned on a line in X direction and (X0,Y0) is an offset. Detection of all beamlets with a single detector and subsequent demodulation at a sum frequency of nM and $\Omega$, or multiples of it, e.g. nM+$\Omega$, yields the photothermal signal from sample position (nX+X0,Y0).

Infrared-Optical Hybrid Imaging without Reference Measurement

A modulation of the heating beam can be introduced in order to provide a differential measurement between the presence and absence of a photothermal expansion. This method removes the need of a reference measurement. Temporal modulation describes an intensity modulation of the heating beam in time that is applied to the entire beam. The simplest case is a step function where the heating beam is switched on and the photothermal expansion is observed in time. Periodic intensity modulations at a single frequency periodically switch the heating beam on and off at frequency $\Omega$ (square wave form) or periodically drive the intensity between on and off states at frequency $\Omega$ (e.g. sine wave, triangular wave form). Such periodic modulations at a single frequency $\Omega$ enable demodulation techniques to be applied to recover the photothermal signal and have an SNR advantage over a direct differential measurement. Arbitrary periodic waveforms are possible, and also waveforms including more than one frequency. For example, periodic intensity modulations can be achieved by using an optical chopper, by operating the light source in pulsed mode, or by using a Fourier Transform Interferometer (FTIR). The latter would allow encoding several frequencies in a single measurement similar to FTIR spectroscopy.

Spatial modulation of the heating beam describes a temporal modulation of the beam in a way that the illuminating pattern of the beam at the sample changes in time. This could be achieved by a spatial modulation in real space where individual locations of the heating beam on the sample are intensity modulated, as described above. Alternatively, the individual plane waves that compose the illuminating heating beam are intensity modulated individually. In this case, the individual k vectors of the illuminating beam are intensity modulated. For example, the heating beam could be focused to a line on the sample with a cylindrical lens. Using a galvanometer, the line could be translated perpendicularly using a linear-in-time function with frequency S, creating a local intensity modulation at the sample that can be detected by demodulation of the detector signal at the frequency S and higher harmonics nS (n is an integer number). Using a spatial light modulator, the on-off pattern of the spatial light modulator could be imaged onto the sample, allowing for controlling the intensity modulation of the heating beam at each sample position individually. Temporal and spatial modulation can be combined to form a temporal-spatial modulation approach.

Multi-Frequency Heating Beam

Some of the embodiments disclosed herein can be implemented using a multi-frequency heating beam. The frequency of the heating beam is stepped, and data acquisition is repeated for each wavelength point to obtain a photothermal point spectrum (for point-scanning modalities) or a spectral data cube (x, y, lambda; for wide-field modalities).

Alternatively, a multi-frequency heating beam could be employed where each frequency f_i is intensity modulated at a different frequency $\Omega$_i. This is conceivably easy to achieve with state-of-the-art quantum cascade lasers, which include several chips in a single housing that can be addressed individually. Photothermal images are then obtained by double demodulation, for example first acquiring a single data set and then demodulating the signal at the individual frequencies $\Omega$_i.

Method for Imaging a Response of a Sample to Radiative Heating

Figure 4:
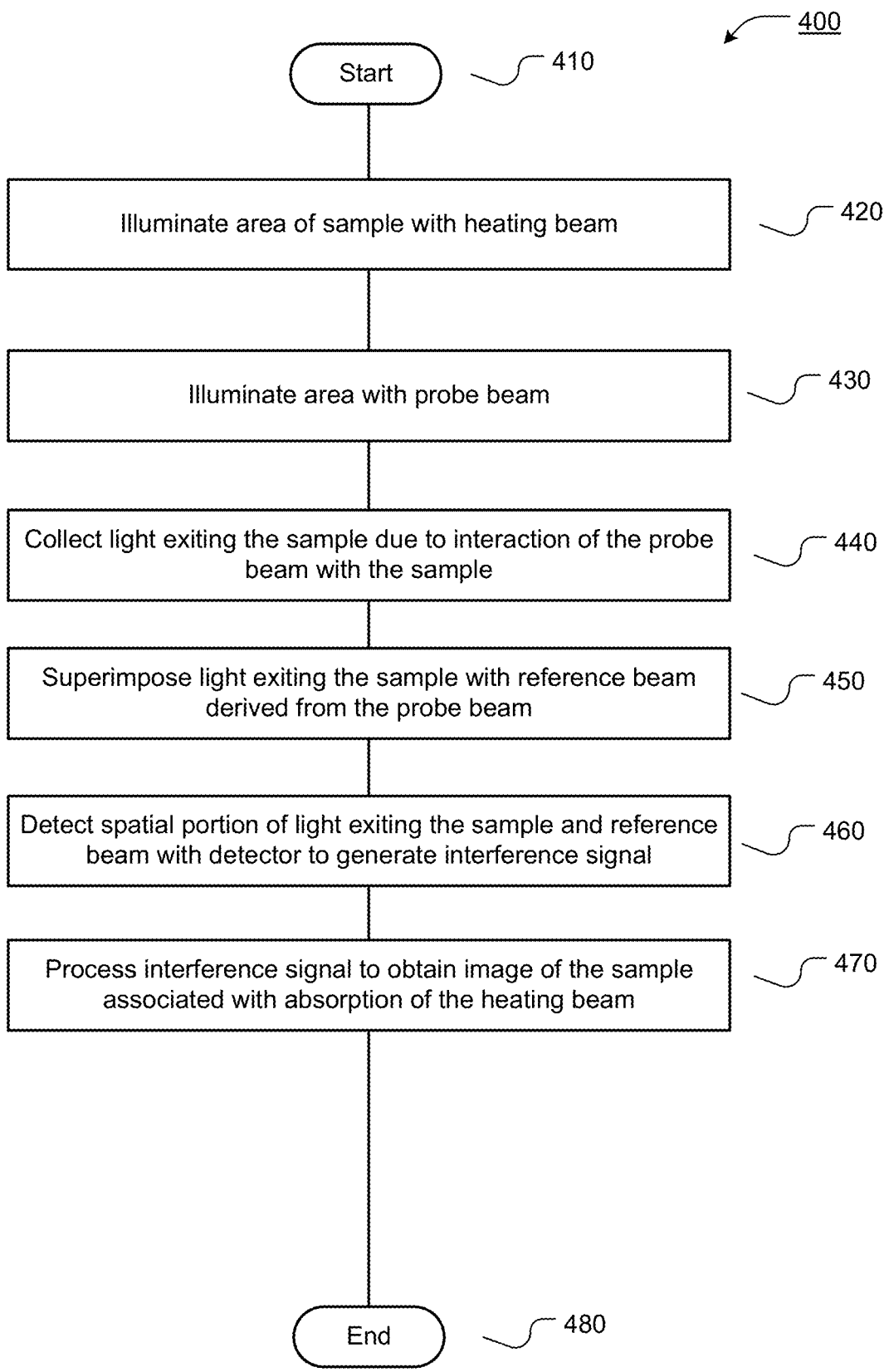
FIG. 4 shows a method for imaging a response of a sample to radiative heating in accordance with an embodiment of the present invention.

FIG. 4 depicts a method for imaging a response of a sample to radiative heating in accordance with an embodiment of the present invention. The method begins at step 410.

The method then proceeds to step 420, where a first area of the sample is illuminated with a radiative heating beam, as described in detail above with reference to FIGS. 1 and 3. The radiative heating beam may be characterized by a wavelength at least as long as mid-IR. The radiative heating beam may also be temporally swept in frequency to obtain a spectrum. The heating beam may further be modulated temporally, spatially, or temporally and spatially. If the heating beam is modulated in time, it may be modulated at a modulation rate exceeding the frame rate of the camera associated with the detector.

The method continues at step 430, where a portion of the first area of the sample is illuminated with a probe beam, as described in detail above with reference to FIGS. 1 and 3. The interaction of the probe beam and the sample may result in scattering of the probe beam, reflection of the probe beam off the sample, or transmission of the probe beam through the sample. The probe beam may be characterized by a wavelength shortward of 3 µm. The probe beam may further be of low coherence. Illuminating the sample with the probe beam may also include focusing the probe beam to a focus.

The portion of the first area of the sample illuminated by the probe beam may be a contiguous portion. However, it may also include multi-focal point sub-portions. In addition, the portion of the first area illuminated with the probe beam may be varied as a function of time. A focus of the probe beam may be translated in such a manner as to vary the portion of the first area illuminated as a function of time. The heating beam illuminating the first area of the sample and the probe beam illuminating a portion of the first area may, at least in part, use common optics, such as a microscope objective.

The method then proceeds to step 440, where light exiting the sample due to interaction of the probe beam with the sample is collected, as described in detail above with reference to FIGS. 1 and 3. The light exiting the sample may be coupled toward a detector via optics that are common at least in part with optics though which the portion of the first area of the sample is illuminated. Such optics may, for example, include a microscope objective.

In step 450, the light exiting the sample is superimposed with a reference beam derived from the probe beam, wherein the reference beam is characterized by an optical phase relative to the probe beam. The reference beam may traverse a portion of the sample. This step may also include imposing a specified phase shift, a specified frequency shift, or both, on the reference beam as a function of time. Imposing a specified phase shift may include imposing a path length difference in a path traversed by the reference beam relative to the light exiting the sample.

The method continues at step 460, where a spatial portion of the light exiting the sample and the reference beam are detected with at least one detector to generate an interference signal, as described in detail above with reference to FIGS. 1 and 3. The at least one detector may include a camera. Detecting a spatial portion of the light exiting the sample may include focusing a reflected or scattered probe beam to a focus on a single detector, such as a camera. The detected spatial portion of the light may vary as a function of time.

The method then proceeds to step 470, where the interference signal is processed to obtain an image of the sample associated with absorption of the radiative heating beam, as described in detail above with reference to FIGS. 1 and 3. The processing may further include identifying a cell type on the basis of a measured molecular-specific response of the sample to radiative heating. The method ends at step 480.

Application in All-Digital Histopathology

Figure 5:
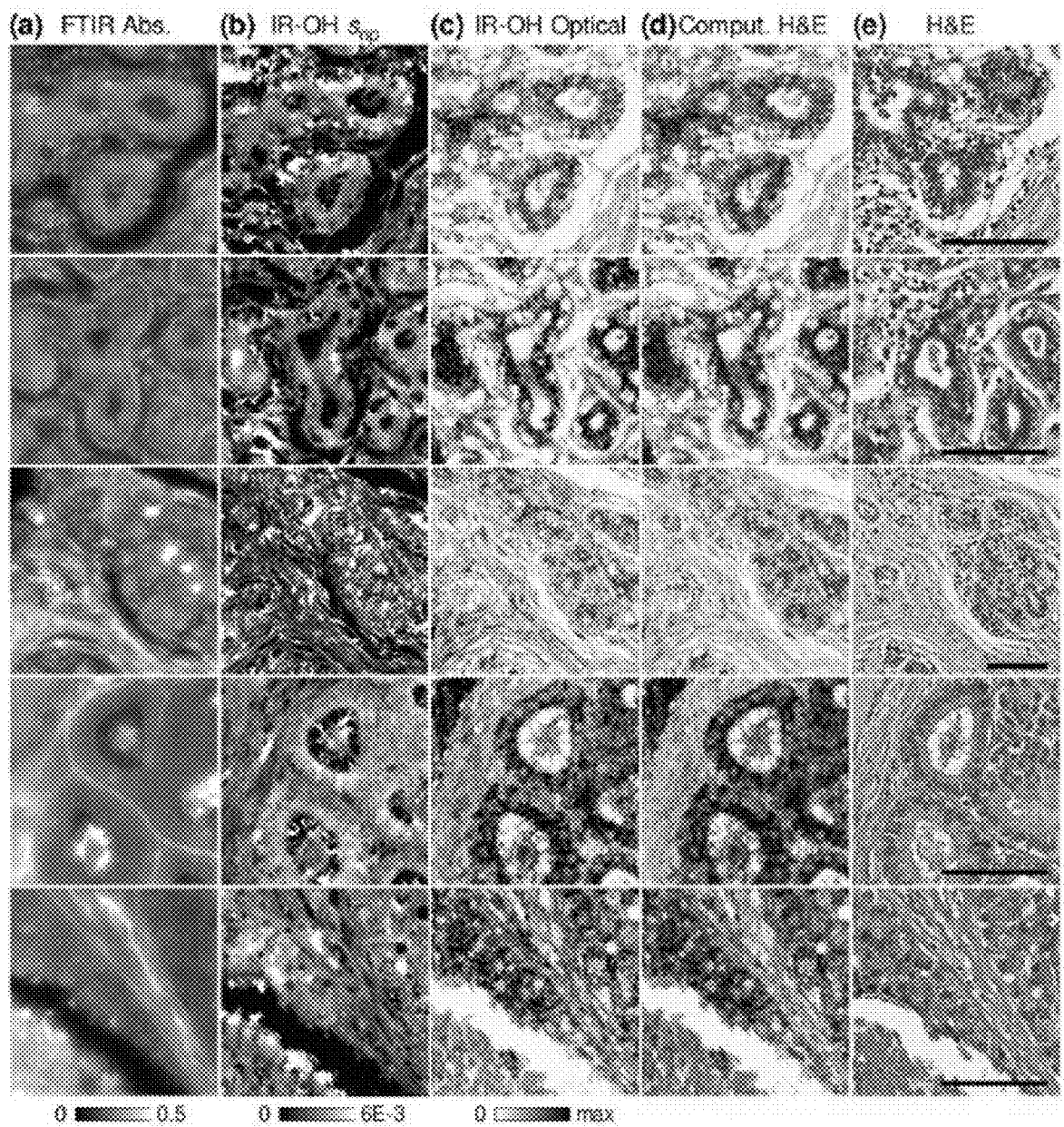
FIG. 5 shows an application of embodiments of the present invention to achieve all-digital histopathology for tissue biopsy samples.

FIG. 5 shows an application of embodiments disclosed herein to achieve all-digital histopathology for tissue biopsy samples. Photothermal imaging at one or more frequencies of the heating beam yield a spectroscopic data set where at each pixel spectral information is obtained on the sample. Such data set could be acquired, for example, by sequential stepping of the heating beam frequency. FIG. 5 (*a*) shows the uncorrected absorbance from FTIR spectroscopy (at 1550 cm$^{-1}$) with limited contrast due to limited optical resolving power and scattering. FIG. 5 (*b*) depicts the infrared-optical hybrid absorption (1550 cm$^{-1}$). Part (c) of FIG. 5 shows low-coherence interferometry images from the optical channel that are co-registered to those in (b). FIG. 5 (*d*) shows a computed, i.e. all-digital, image using the stainless staining approach that mimics conventional H&E (hematoxylin and eosin) staining. Finally, FIG. 5 (*e*) depicts conventional H&E images of an adjacent tissue section. Analysis of the spectroscopic data set, e.g. the one visualized in FIG. 5 (*d*), on a computer determines and spatially resolves cell types and disease state. Exemplarily, this could be achieved by using machine learning as described in Fernandez et al., "*Infrared spectroscopic imaging for histopathologic recognition*", *Nature Biotechnology* 23, 469-474 (2005), which is incorporated herein by reference in its entirety.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for imaging a response of a sample to radiative heating, the method comprising:
   a. illuminating a first area of the sample with a radiative heating beam characterized by a wavelength longer than 2.5 µm;
   b. illuminating a portion of the first area with a probe beam, wherein the probe beam is characterized by a wavelength shorter than 3 µm;
   c. collecting light exiting the sample due to interaction of the probe beam with the sample;
   d. superimposing the light exiting the sample with a reference beam derived by imposing a phase shift on the probe beam to produce a combined light beam;
   e. detecting a spatial portion of the combined light beam with at least one camera to generate a multidimensional array of interference signals; and
   f. processing the array of interference signals to obtain an image of the sample associated with absorption of the radiative heating beam.

2. A method in accordance with claim 1, wherein the at least one camera includes a high full well capacity CMOS camera and wherein the interference signals have a signal-to-noise ratio of at least 100:1.

3. A method in accordance with claim 1, wherein the reference beam traverses a portion of the sample.

4. A method in accordance with claim 1, wherein interaction of the probe beam with the sample includes at least one of scattering, reflection and transmission of the probe beam.

5. A method in accordance with claim 1, wherein the radiative heating beam is temporally swept in frequency to obtain a spectrum.

6. A method in accordance with claim 1, wherein the radiative heating beam is provided as an evanescent wave at the sample.

7. A method in accordance with claim 1, wherein illuminating a first area of the sample with a radiative heating beam comprises modulating the radiative heating beam at least one of temporally and spatially.

8. A method in accordance with claim 1, wherein illuminating a portion of the first area with a probe beam includes focusing the probe beam to a focus.

9. A method in accordance with claim 1, wherein detecting a spatial portion of the combined light beam includes focusing a reflected or scattered beam to a focus on a single detector.

10. A method in accordance with claim 9, wherein the at least one detector includes a camera.

11. A method in accordance with claim 1, wherein the portion of the first area illuminated with a probe beam is a contiguous portion.

12. A method in accordance with claim 1, wherein the portion of the first area illuminated with a probe beam includes multi-focal point sub-portions.

13. A method in accordance with claim 1, wherein the portion of the first area illuminated with a probe beam is varied as a function of time.

14. A method in accordance with claim 1, further comprising translating a focus of the probe beam in such a manner as to vary the portion of the first area illuminated as a function of time.

15. A method in accordance with claim 1, wherein the detected spatial portion of the combined light beam is varied as a function of time.

16. A method in accordance with claim 1, wherein the heating beam is modulated in time.

17. A method in accordance with claim 16, wherein the heating beam is modulated in time at a heating beam modulation rate exceeding a camera frame rate associated with the detector.

18. A method in accordance with claim 1, wherein the probe beam is of low coherence.

19. A method in accordance with claim 1, wherein the first area of the sample is illuminated by the heating beam and the portion of the first area of the sample is illuminated by the probe beam via optics that are common at least in part.

20. A method in accordance with claim 1, wherein the combined light beam is coupled toward a detector via optics that are common at least in part with optics through which the portion of the first area of the sample is illuminated.

21. A method in accordance with claim 19, wherein the optics include a microscope objective.

22. A method in accordance with claim 1, wherein imposing a phase shift comprises imposing a path length difference in a path traversed by the reference beam relative to the light exiting the sample.

23. A method in accordance with claim 1, wherein a spatial portion of the combined light beam is detected for at least two different phase shifts of the reference beam.

24. A method in accordance with claim 1, wherein processing the interference signal includes demodulation of the interference signal at a frequency associated to said specified phase shift.

25. A method in accordance with claim 1, wherein the heating beam is processed in time and processing the interference signal includes demodulation of the interference signal at a frequency associated to said phase shift and the time-modulation of the heating beam.

26. A method in accordance with claim 1, further comprising identifying a cell type of the basis of a measured molecular-specific response of the sample to radiative heating.

27. An apparatus for wide-field photothermal measurements of a sample, the apparatus comprising:
   a. a first source for generating a radiative heating beam at a wavelength longer than 2.5 µm;
   b. a second source for generating a probe beam at a wavelength shorter than 3 µm;
   c. a first optical arrangement for coupling the radiative heating beam onto a first area of the sample;
   d. a second optical arrangement for coupling the probe beam onto a portion of the first area of the sample;
   e. a phase shifter for imposing a phase shift on the probe beam to create a reference beam;
   f. an interferometer for superimposing light exiting the sample with the reference beam to produce a combined light beam;
   g. a camera for detecting a spatial portion of the combined light beam to generate a multidimensional array of interference signals; and
   h. a processor for the array of interference signals to obtain an image of the sample associated with absorption of the radiative heating beam.

28. An apparatus in accordance with claim 27, wherein the camera is a high full well capacity CMOS camera and wherein the interference signals have a signal-to-noise ratio of at least 100:1.

29. An apparatus in accordance with claim 27, wherein the phase shift corresponds to a path length difference imposed between the reference beam and the probe beam.

30. An apparatus in accordance with claim 27, wherein the second source is a low-coherence source.

31. An apparatus in accordance with claim 30, wherein the low-coherence source is chosen from a group of low-coherence sources including superluminescent diodes, light-emitting diodes, supercontinuum lasers and picosecond lasers.

32. An apparatus in accordance with claim 27, wherein the interferometer is chosen from a group of interferometer configurations including Michelson, Mach-Zehnder, Mirau and Linnik interferometers.

33. An apparatus for confocal photothermal measurements of a sample, the apparatus comprising:
   a. a first source for generating a radiative heating beam at a wavelength longer than 2.5 µm;
   b. a second source for generating a probe beam at a wavelength shorter than 3 µm;
   c. a first optical arrangement for coupling the radiative heating beam onto a first area of the sample;
   d. a second optical arrangement for coupling the probe beam onto a portion of the first area of the sample and focusing the probe beam to at least one focus;
   e. a phase shifter for imposing a phase shift on the probe beam to create a reference beam;
   f. an interferometer for superimposing light exiting the sample with the reference beam to produce a combined light beam;
   g. a photodetector for detecting a spatial portion of the combined light beam exiting the sample to generate interference signals; and
   h. a processor for the interference signals to obtain measurements associated with absorption of the radiative heating beam.

34. An apparatus in accordance with claim 33, wherein a scanning mechanism for sequentially scanning a position of the probe beam relative to the sample; and the processor for the interference signal to obtain an image of the sample associated with absorption of the radiative heating beam.

35. An apparatus in accordance with claim 33, wherein the phase shift corresponds to a path length difference imposed between the reference beam and the probe beam.

36. An apparatus in accordance with claim 33, wherein the second source is a low-coherence source.

37. An apparatus in accordance with claim 36, wherein the low-coherence source is chosen from a group of low-coherence sources including superluminescent diodes, light-emitting diodes, supercontinuum lasers and picosecond lasers.

38. An apparatus in accordance with claim 36, wherein the processor for the interference signal is configured to obtain tomographic measurements associated with absorption of the radiative heating beam.

39. An apparatus in accordance with claim 33, wherein the second source is a frequency-tunable monochromatic source and the processor for the interference signal is configured to obtain tomographic measurements associated with absorption of the radiative heating beam.

40. An apparatus in accordance with claim 33, wherein the second source is a low-coherence source; and wherein the detector further comprises an optical dispersion device to select at least one wavelength; a processor for the interference signal to obtain tomographic measurements associated with absorption of the radiative heating beam.

41. A method in accordance with claim 2, wherein the camera has a full well capacity of more than 100,000 electrons per pixel and is configured to operate at a frame rate greater than 100 Hz.

42. An apparatus in accordance with claim 27, wherein the first source is configured to modulate the radiative heating beam at a frequency Q, wherein the phase shifter is configured to yield a fringe frequency S, and wherein the processor is further configured to demodulate the array of interference signals at a frequency $n*\Omega+m*S$, wherein n is a positive integer and m is a negative or positive integer.

43. An apparatus in accordance with claim 27, wherein the first source is configured to modulate the radiative heating beam at a frequency $\Omega$, wherein the second source is configured to modulate the probe beam at a frequency P greater than a frame rate of the camera, and wherein the processor is further configured to demodulate the array of interference signals at a low-frequency alias $\Omega'$ of the frequency $\Omega$.

44. A method in accordance with claim 1, wherein imposing a phase shift on the reference beam includes at least one of reflecting the reference beam from a movable mirror and translating the sample along an optical axis.

45. A method in accordance with claim 1, wherein imposing a phase shift on the reference beam includes imparting a spatial pattern of phase shifts between the reference beam and the light exiting the sample due to interaction of the probe beam with the sample.

46. A method in accordance with claim 1, wherein the radiative heating beam is modulated at a frequency $\Omega$ and wherein processing the array of interference signals includes demodulating the interference signals at a frequency related to $\Omega$.

47. A method in accordance with claim 46, wherein the radiative heating beam is modulated at a frequency $\Omega$, wherein imposing a phase shift on the reference beam causes production of a fringe frequency S in the interference signal, and wherein processing the array of interference signals includes demodulating the interference signals at at least one of a frequency $S-\Omega$ and a frequency $S+\Omega$.

48. A method in accordance with claim 1, wherein the radiative heating beam is modulated at a frequency $\Omega$, wherein the probe beam is modulated in intensity at the frequency $\Omega$ and with a phase shift relative to the modulation of the radiative heating beam, and wherein the spatial portion of the light exiting the sample and the reference beam is detected at a sampling frequency F lower than the frequency $\Omega$.

49. A method in accordance with claim 48, wherein processing the array of interference signals includes demodulating the interference signals at a frequency related to a low-frequency alias of the modulation frequency $\Omega$ with reference to the sampling rate F.

50. A method in accordance with claim 1, wherein the portion of the first area of the sample is illuminated by the heating beam via first optics and the light exiting the sample due to interaction of the probe beam with the sample is collected via second optics that are spatially separated from the first optics.

51. A method in according with claim 50, wherein the first area of the sample is illuminated by the heating beam with optics transparent to the heating beam selected from the group of reflective optics, refractive optics, and combinations thereof, and wherein light exiting the sample due to interaction of the probe beam with the sample is collected with refractive optics transparent to the probe beam.

52. An apparatus in accordance with claim 27, wherein the camera is configured to detect a plurality of frames, wherein the camera is configured to detect one camera frame for each specific configuration of the phase shifter, and wherein the camera is further configured to generate the multidimensional array of interference signals from the plurality of frames.

53. An apparatus in accordance with claim 27, wherein the phase shifter comprises at least one of a movable mirror and a movable sample stage.

54. An apparatus in accordance with claim 27, wherein an optical system for collection of the light exiting the sample due to interaction of the probe beam with the sample is spatially separated from the first optical arrangement for coupling the radiative heating beam onto a first area of the sample.

55. An apparatus in accordance with claim 54, wherein the interferometer is arranged within a microscope objective assembly.

56. A method in accordance with claim 1, wherein the at least one camera includes a high-speed camera that has a full well capacity of at least 10,000 electrons per pixel and wherein the at least one camera is configured to operate at a frame rate of at least 10,000 Hz.

57. A method in accordance with claim 1, wherein the probe beam is generated by spatially incoherent light source.

58. An apparatus in accordance with claim 27, wherein the second source is spatially incoherent.

59. A method in accordance with claim 1, wherein imposing a specified phase shift on the reference beam includes sweeping the frequency of the probe beam.

60. An apparatus in accordance with claim 33, wherein the phase shifter comprises at least one of a movable mirror and a movable sample stage.

* * * * *